United States Patent [19]

Berg et al.

[11] Patent Number: 4,948,469

[45] Date of Patent: Aug. 14, 1990

[54] SEPARATION OF FORMIC ACID FROM DIOXANE BY EXTRACTIVE DISTILLATION WITH AMIDES

[75] Inventors: Lloyd Berg; Richard R. Rall, both of 1314 S. Third Ave., Bozeman, Mont. 59715

[73] Assignee: Lloyd Berg, Bozeman, Mont.

[21] Appl. No.: 279,918

[22] Filed: Dec. 5, 1988

[51] Int. Cl.$^5$ ............... B01D 3/40; C07C 53/02; C07D 319/12

[52] U.S. Cl. ............ 203/51; 203/56; 203/60; 203/61; 203/62; 203/63; 203/64; 549/377; 562/609

[58] Field of Search ......... 203/60, 51, 61, 63, 203/64, 62, 65, 56; 549/377; 562/609

[56] References Cited

U.S. PATENT DOCUMENTS

| | | |
|---|---|---|
| 2,441,114 | 5/1948 | Krieble et al. ............ 549/377 |
| 4,007,095 | 2/1977 | Wolf et al. ............ 549/377 |
| 4,285,881 | 8/1981 | Yang ............ 549/377 |
| 4,801,358 | 1/1989 | Berg et al. ............ 203/62 |

FOREIGN PATENT DOCUMENTS

| | | | |
|---|---|---|---|
| 44-29858 | 2/1969 | Japan | 549/377 |
| 49-54324 | 5/1974 | Japan | 562/608 |
| 55-85584 | 6/1980 | Japan | 549/377 |
| 967471 | 12/1960 | United Kingdom | 203/60 |
| 2172887 | 10/1986 | United Kingdom | 549/377 |

*Primary Examiner*—Wilbur Bascomb

[57] ABSTRACT

Dioxane cannot be completely removed from dioxane and formic acid mixtures by distillation because of the presence of the maximum azeotrope. Dioxane can be readily removed from dioxane - formic acid mixtures by extractive distillation in which the extractive agent is dimethylformamide, dimethylacetamide or these with certain high boiling organic compounds.

2 Claims, No Drawings

SEPARATION OF FORMIC ACID FROM DIOXANE BY EXTRACTIVE DISTILLATION WITH AMIDES

FIELD OF THE INVENTION

This invention relates to a method for separating formic acid from dioxane using certain dimethyl amides as the agent in extractive distillation.

DESCRIPTION OF PRIOR ART

Extractive distillation is the method of separating close boiling compounds or azetropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile component of the close boiling mixtures and the extractive agent are continuously removed from the column. The usual methods of separation of these two components are the use of another rectification column, cooling and phase separation or solvent extraction.

Formic acid, B.P.=100.8° C., and dioxane, B.P.=101.4° C. form a maximum azeotrope boiling at 113.4° C. and containing 43 wt.% formic acid. When these two are found together in mixtures, either alone or with other liquids, distillation will only produce the azeotrope, never pure formic acid or dioxane. Thus any liquid mixture containing these two will upon distillation produce the azeotrope. Extractive distillation would be an attractive method of effecting the separation of formic acid from dioxane if agents can be found that (1) will break the formic acid - dioxane azeotrope and (2) are easy to recover from the formic acid, that is, form no azeotrope with formic acid and boil sufficiently above formic acid to make the separation by rectification possible with only a few theoretical plates.

Extractive distillation typically requires the addition of an equal amount to twice as much extractive agent as the formic acid - dioxane on each plate of the rectification column. The extractive agent should be heated to about the same temperature as the plate on to which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

OBJECTIVE OF THE INVENTION

The object of this invention is to provide a process or method of extractive distillation that will enhance the relative volatility of dioxane from formic acid in their separation in a rectification column. It is a further object of this invention to identify suitable extractive distillation agents will eliminate the formic acid - dioxane azeotrope and make possible the production of pure formic acid and ioxane by rectification. It is a further object of this invention to identify certain amides which in addition to the above constraints, are stable, can be separated from formic acid by rectification with relatively few theoretical plates and can be recycled to the extractive distillation column and reused with little or no decomposition.

SUMMARY OF THE INVENTION

The objects of the invention are provided by a process for separating formic acid from dioxane which entails the use of dimethylacetamide or dimethylformamide, either alone or admixed with certain oxygenated organic compounds as the agents in extractive distillation.

TABLE 1

Extractive Distillation Agents Which Are Effective In Breaking The Formic Acid - Dioxane Azeotrope

| Compounds | Ratios | | Relative Volatility | |
|---|---|---|---|---|
| Dimethylformamide (DMFA), Adipic Acid | $(1/2)^2$ | $(3/5)^2$ | 1.2 | 1.6 |
| DMFA, Acetyl salicylic acid | " | " | 1.8 | 2.5 |
| DMFA, Azelaic acid | " | " | 3.9 | 4.2 |
| DMFA, Benzoic acid | " | " | 1.6 | 2.1 |
| DMFA, p-tert. Butyl benzoic acid | " | " | 4.0 | 3.5 |
| DMFA, Cinnamic acid | " | " | 3.3 | 2.2 |
| DMFA, Decanoic acid | " | " | 1.6 | 1.6 |
| DMFA, Dodecanedioic acid | " | " | 4.4 | 5.2 |
| DMFA, Glutaric Acid | " | " | 2.0 | 2.1 |
| DMFA, Heptanoic acid | " | " | 2.6 | 3.4 |
| DMFA, Hexanoic acid | " | " | 2.3 | 4.0 |
| DMFA, 4-Hydroxybenzoic acid | " | " | 4.4 | 3.1 |

TABLE 1-continued

Extractive Distillation Agents Which Are Effective In Breaking The Formic Acid - Dioxane Azeotrope

| Compounds | Ratios | | Relative Volatility | |
|---|---|---|---|---|
| DMFA, Itaconic acid | " | " | 2.5 | 2.1 |
| DMFA, Malic acid | " | " | 2.5 | 2.4 |
| DMFA, Neodecanoic acid | " | " | 2.5 | 1.2 |
| DMFA, Octanoic acid | " | " | 2.0 | 3.0 |
| DMFA, Pelargonic acid | " | " | 2.4 | 5.2 |
| DMFA, Salicylic acid | " | " | 1.1 | 4.9 |
| DMFA, Sebacic acid | " | " | 1.2 | 2.4 |
| DMFA, o-Toluic acid | " | " | 4.2 | 5.4 |
| DMFA, m-Toluic acid | " | " | 2.1 | 1.7 |
| DMFA, p-Toluic acid | " | " | 2.1 | 6.2 |
| DMFA, Glycerol triacetate | " | | 1.7 | |
| DMFA, Ethylene glycol butyl ether acetate | " | | 1.2 | |
| DMFA, Hexylene glycol diacetate | " | | 1.2 | |
| DMFA, Ethylene glycol diacetate | " | | 2.5 | |
| DMFA, Diethylene glycol ethyl acetate | " | | 2.3 | |
| DMFA, Butoxypropanol | " | | 3.3 | |
| DMFA, Propoxypropanol | " | | 4.7 | |
| DMFA, Dipropylene glycol methyl ether | " | | 1.8 | |
| DMFA, Isobornyl acetate | " | | 1.8 | |
| DMFA, Adipic acid, Methyl salicylate | $(1/3)^3$ | $(2/5)^3$ | 1.8 | 1.7 |
| DMFA, Acetyl salicylic acid, Cyclohexanone | " | " | 2.7 | 3.9 |
| DMFA, Azelaic acid, Ethylene glycol diacetate | " | " | 4.2 | 1.5 |
| DMFA, Benzoic acid, Isophorone | " | " | 1.6 | 2.6 |
| DMFA, p-tert. Butyl benzoic acid, 2-Methoxy-ethyl ether | " | " | 3.8 | 4.8 |
| DMFA, Cinnamic acid, Anisole | " | | 1.3 | |
| DMFA, Decanoic acid, Acetophenone | " | " | 1.6 | 1.7 |
| DMFA, Dodecanedioic acid, Dipropylene glycol dimethyl ether | " | " | 1.8 | 1.8 |
| DMFA, Glutaric acid, Butyl ether | $(1/3)^3$ | $(2/5)^3$ | 2.5 | 3.2 |
| DMFA, Heptanoic acid, Ethyl benzoate | " | " | 4.1 | 6.2 |
| DMFA, Hexanoic acid, Methyl benzoate | " | " | 2.1 | 3.4 |
| DMFA, 4-Hydroxybenzoic acid, Propylene glycol dimethyl ether | " | " | 1.4 | 4.2 |
| DMFA, Itaconic acid, Methyl phenyl acetate | " | " | 2.5 | 1.3 |
| DMFA, Malic acid, Diethylene glycol dibenzoate | " | " | 1.2 | 1.5 |
| DMFA, Necdecanoic acid, Adiponitrile | " | " | 3.1 | 1.5 |
| DMFA, Octanoic acid, Butyl benzoate | " | " | 3.3 | 2.3 |
| DMFA, Pelargonic acid, Benzyl benzoate | " | " | 1.8 | 2.6 |
| DMFA, Salicyl acid, Phenetol | " | " | 1.6 | 2.4 |
| DMFA, Sebacic acid, Benzyl ether | " | " | 2.7 | 1.5 |
| DMFA, o-Toluic acid, Diethylene glycol diethyl ether | " | " | 4.7 | 3.3 |
| DMFA, o-Toluic acid, Diethylene glycol ethyl ether | " | " | 4.2 | 1.8 |
| DMFA, p-Toluic acid, Dipropylene glycol dibenzoate | " | " | 2.9 | 2.1 |
| Dimethylacetamide (DMAA) | 1 | | 1.7 | |
| DMAA, Azelic acid | $(1/2)^2$ | $(3/5)^2$ | 1.5 | 3.3 |
| DMAA, Acetyl salicylic acid | " | " | 2.7 | 1.7 |
| DMAA, Benzoic acid | " | " | 1.4 | 2.3 |
| DMAA, p-tert. Butyl benzoic acid | " | " | 2.1 | 3.2 |
| DMAA, Cinnamic acid | " | " | 2.7 | 2.3 |
| DMAA, Decanoic acid | " | " | 5.1 | 4.5 |
| DMAA, Dodecanedioc acid | " | " | 2.1 | 3.0 |
| DMAA, Glutaric acid | " | " | 2.6 | 2.5 |
| DMAA, Heptanoic acid | " | " | 1.6 | 3.8 |
| DMAA, Hexanoic acid | " | " | 3.5 | 2.5 |
| DMAA, p-Hydroxybenzoic acid | " | " | 3.5 | 1.9 |
| DMAA, Itaconic acid | " | " | 3.6 | 2.7 |
| DMAA, Malic acid | " | " | 2.3 | 1.9 |
| DMAA, Octanoic acid | " | " | 1.3 | 2.2 |
| DMAA, Salicylic acid | " | " | 1.1 | 1.7 |
| DMAA, Sebacic acid | " | " | 1.6 | 2.0 |
| DMAA, o-Toluic acid | " | " | 2.1 | 4.3 |
| DMAA, m-Toluic acid | " | " | 2.1 | 1.8 |
| DMAA, p-Toluic acid | " | " | 1.3 | 2.1 |
| DMAA, Adipic acid | " | " | 2.1 | 1.5 |
| DMAA, Adipic acid, Benzyl benzoate | $(1/3)^3$ | $(2/5)^3$ | 2.2 | 1.6 |
| DMAA, Acetyl salicylic acid, Butyl benzoate | " | " | 2.2 | 2.2 |
| DMAA, Axelaic acid, Isophorone | " | " | 2.4 | 2.2 |
| DMAA, Benzoic acid, Cyclohexanone | " | " | 3.7 | 2.4 |
| DMAA, p-tert. Butyl benzoic acid, Benzyl ether | " | " | 1.8 | 1.8 |
| DMAA, Cinnamic acid, Diethylene glycol diethyl ether | " | " | 2.2 | 2.2 |
| DMAA, Decanoic acid, Ethyl benzoate | " | " | 2.9 | 1.2 |
| DMAA, Dodecanedioic acid, Anisole | " | " | 2.1 | 1.4 |
| DMAA, Glutaric acid, Butyl ether | $(1/3)^3$ | $(2/5)^3$ | 4.6 | 1.5 |
| DMAA, Heptanoic acid, Acetophone | " | " | 2.0 | 2.1 |
| DMAA, Hexanoic acid, Adiponitrile | " | " | 4.6 | 2.9 |
| DMAA, p-Hydroxybenzoic acid, 2-Octanone | " | " | 1.8 | 1.5 |
| DMAA, Itaconic acid, Dipropylene glycol dibenzoate | " | " | 2.1 | 1.5 |

TABLE 1-continued

Extractive Distillation Agents Which Are Effective In Breaking The Formic Acid - Dioxane Azeotrope

| Compounds | Ratios | | Relative Volatility | |
| --- | --- | --- | --- | --- |
| DMAA, Malic acid, 2-Methoxy ethyl ether | " | " | 1.4 | 1.4 |
| DMAA, Octanoic acid, Methyl benzoate | " | " | 2.7 | 2.5 |
| DMAA, Salicylic acid, Methyl salicylate | " | " | 1.5 | 1.5 |
| DMAA, o-Toluic acid, Methyl penyl acetate | " | " | 2.9 | 2.2 |
| DMAA, m-toluic acid, Ethyl phenyl acetate | " | " | 1.7 | 3.2 |
| DMAA, p-Toluic acid, Anisole | " | " | 1.9 | 1.5 |

TABLE 2

Data From Runs Made In Rectification Column

| Agent | Column | Time Hrs. | Weight % Dioxane | Weight % Formic acid | Relative Volatility |
| --- | --- | --- | --- | --- | --- |
| 50% Dimethylformamide | Overhead | 0.5 | 80.8 | 19.2 | 1.72 |
| 50% Propoxypropanol | Bottoms | | 26.8 | 73.2 | |
| 50% Propoxypropanol | Overhead | 1.5 | 81.5 | 18.5 | 1.58 |
| 50% Propoxypropanol | Bottoms | | 36.4 | 63.6 | |
| Dimethylacetamide | Overhead | 0.75 | 88.6 | 11.4 | 1.71 |
| | Bottoms | | 30.8 | 69.2 | |
| Dimethylacetamide | Overhead | 1.5 | 90.4 | 9.6 | 1.71 |
| | Bottoms | | 36.8 | 63.2 | |

DETAILED DESCRIPTION OF THE INVENTION

We have discovered that dimethylacetamide and dimethylformamide, either alone or admixed with other organic compounds, will effectively negate the formic acid - dioxane azeotrope and permit the separation of pure dioxane from formic acid by rectification when employed as the agent in extractive distillation. Table 1 lists dimethylformamide, dimethylacetamide and their mixtures in the proportions that we have found to be effective. The data in Table 1 was obtained in a vapor-liquid equilibrium still. In each case, the starting material was the formic acid - dioxane azeotrope. The ratios are the parts by weight of extractive agent used per part of formic acid - dioxane azeotrope. The relative volatilities are listed for each of the two ratios employed. The compounds which are effective when used in mixtures with dimethylformamide or dimethylacetamide are adipic acid, acetyl salicyclic acid, azelaic acid, benzoic acid, p-tertiary butyl benzoic acid, cinnamic acid, decanoic acid, dodecanedioic acid, glutaric acid, heptanoic acid, hexanoic acid, 4-hydroxybenzoic acid, itaconic acid, malic acid, neodecanoic acid, octanoic acid, pelargonic acid, salicyclic acid, sebacic acid, o-toluic acid, m-toluic acid, p-toluic acid, glycerol triacetate, ethylene glycol butyl ether acetate, hexylene glycol diacetate, ethylene glycol diacetate, diethylene glycol ethyl ether acetate, butoxypropanol, proxypropanol, methyl salicylate, dipropylene glycol methyl ether, isobornyl acetate, cyclohexanone, isophorone, 2-methoxy ethyl ether, anisole, acetophenone, dipropylene glycol dimethyl ether, butyl ether, methyl benzoate, ethyl benzoate propylene glycol dimethyl ether, methyl phenyl acetate, diethylene glycol dibenzoate, adionitrile, butyl benzoate, benyl benzoate, phenetol, benzyl ether, diethylene glycol diethyl ether, diethylene glycol ethyl ether, dipropylene glycol dibenzoate, 2-octanone, 2-methoxy ethyl ether and ethyl phenyl acetate. The two relative volatilities shown in Table 1 correspond to the two different ratios investigated. For example, in Table 1, one-half part of dimethylformamide plus one-half part of azelaic acid with one part of the formic acid - dioxane azeotrope gives a relative volatility of 3.9; 3/5 parts of DMFA plus 3/5 parts of azelaic acid give 4.2. One third parts each of dimethylacetamide, benzoic acid and cyclohexanone with one part of the formic acid - dioxane azeotrope gives a relative volatility of 3.7, with two-fifths parts, these three give 2.4. In every example in Table 1, the starting material is the formic acid-dioxane azeotrope which possesses a relative volatility of 1.00.

Two of the agents, dimethylformamide plus propoxypropanol and dimethylacetamide, listed in the Table 1 whose relative volatility had been determined in the vapor-liquid equilibrium still, were then evaluated in a glass perforated plate rectification column possessing 5.2 theoretical plates and the results listed in Table 2. The data in Table 2 was obtained in the following manner. The charge was 250 grams of the formic acid - dioxane azeotrope and after a half hour of operation in the 5.2 theoretical plate column to establish equilibrium, DMFA plus propoxypropanol at 95° C. and 12.5 ml/min. was pumped in. The rectification was continued with the first sampling of the overhead and bottoms after a half hour. The analyses are shown in Table 2 and were overhead 80.8% dioxane, 19.2% formic acid and bottoms 26.8% dioxane, 73.2% formic acid which gives a relative volatility of dioxane to formic acid of 1.72. This indicates that the azeotrope has been negated and separation accomplished. Without the extractive agent, the overhead would have been the azetope composition. This provides that the extractive agent is negating the azeotrope and makes the rectification proceed as if the azeotrope no longer existed thus bringing out the more volatile dioxane as overhead.

THE USEFULNESS OF THE INVENTION

The usefulness or utility of this invention can be demonstrated by referring to the data presented in Tables 1 and 2. All of the successful extractive distillation agents show that dioxane and formic acid can be separated from their maximum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity dioxane and formic acid from any mixture of these two including the maximum azeotrope. The stability of the compounds used and the boiling point difference is such that complete recovery and recycle is obtainable by a simple distillation and the amount required for make-up is small.

WORKING EXAMPLES

Examples 1

Fifty grams of the dioxane - formic acid azeotrope, 25 grams of dimethylformamide (DMFA) and 25 grams of azelaic acid were charged to a vapor-liquid equilibrium still and refluxed for six hours. Analysis indicated a vapor composition of 57.1% dioxane, 42.9% formic acid, a liquid composition of 25.7% dioxane, 74.3% formic acid which is a relative volatility of 3.9. Five grams each of DMFA and azelaic acid were added and refluxing continued for another two hours. Analysis indicated a vapor composition of 59.7% dioxane, 40.3% formic acid, a liquid composition of 25.9% dioxane, 74.1% formic acid which is a relative volatility of 4.2.

Example 2

Fifty grams of the dioxane - formic acid azeotrope, 25 grams of dimethylacetamide (DMAA) and 25 grams of glutaric acid were charged to the vapor-liquid equilibrium still and refluxed for 15 hours. Analysis indicated a vapor composition of 73.2% dioxane, 26.8% formic acid and a liquid composition of 50.9% dioxane, 49.1% formic acid which is a relative volatility of 2.6. Five grams of DMAA and five grams of glutaric acid were added and refluxing continued for another either hours. Analysis indicated a vapor composition of 76.4% dioxane, 23.6% formic acid and a liquid composition of 56.8% dioxane, 43.2% formic acid which is a relative volatility of 2.5.

Example 3

Fifty grams of the dioxane - formic acid azeotrope, 17 grams of DMFA, 17 grams of hexanoic acid and 17 grams of methyl benzoate were charged to the vapor-liquid equilibrium still and refluxed for four hours. Analysis indicated a vapor composition of 60% dioxane, 40% formic acid and a liquid composition of 41.3% dioxane, 58.7% formic acid which is a relative volatility of 2.1. Three grams each of DMFA, hexanoic acid and methyl benzoate were added and refluxing continued for another two hours. Analysis indicated a vapor composition of 70% dioxane, 30% formic acid and a liquid composition of 40.4% dioxane, 59.6% formic acid which is a relative volatility of 3.4.

Example 4

A glass perforated plate rectification column was calibrated with methyl cyclohexane and toluene which possesses a relative volatility of 1.46 and found to have 5.2 theoretical plates. A solution comprising 250 grams of the dioxane - formic acid azeotrope was placed in the stillpot and heated. When refluxing began, an extractive agent comprising 50% DMFA and 50% propoxypropanol was pumped into the column at a rate of 12.5 ml/min. The temperature of the extractive agent as it entered the column was 95° C. After establishing the feed rate of the extractive agent, the heat input to the dioxane and formic acid in the stillpot was adjusted to give a total reflux rate of 50 ml./min. After one-half hour of operation, the overhead and bottoms samples of approximately two ml. were collected and analysed by gas chromatography. The overhead analysis was 80.8% dioxane, 19.2% formic acid. The bottoms analysis was 26.8% dioxane, 73.2% formic acid. Using these compositions in the Fenske equation, with the number of theoretical plates in the column 5.2, gave an average relative volatility of 1.72 for each theoretical plate. After 1.5 hours of continuous operation, the overhead analysis was 81.5% dioxane, 18.5% formic acid, the bottoms analysis was 36.4% dioxane, 63.6% formic acid which is a relative volatility of 1.58.

Example 5

Using the same column and conditions as in Example 4, an extractive agent comprising dimethylacetamide was employed. After three-quarters of an hour of continuous operation, the overhead analysis was 88.6% dioxane, 11.4% formic acid and the bottoms analysis was 30.8% dioxane, 69.2% formic acid which is a relative volatility of 1.71. After 1.5 hours of continuous operation, the overhead analysis was 90.4% dioxane, 9.6% formic acid, the bottoms analysis was 36.8% dioxane, 63.2% formic acid which is a relative volatility of 1.71.

We claim:

1. A method for recovering dioxane from mixtures of dioxane and formic acid which comprises distilling a mixture of dioxane and formic acid in a rectification column in the presence of about one part of an extractive agent per part of dioxane - formic acid mixture, recovering dioxane as overhead product and obtaining the formic acid and the extractive agent from the stillpot, wherein said extractive agent comprises dimethylformamide and at least one material selected from the group consisting of dodecanedioic acid, malic acid, butoxypropanol, diethylene glycol ethyl ether acetate, propoxypropanol, dipropylene glycol methyl ether, isophorone, cyclohexanone, 2-methoxyethyl ether, dipropylene glycol dimethyl ether, propylene glycol dimethyl ether, ethyl phenyl acetate, and diethylene glycol ethyl ether.

2. A method for recovering dioxane from mixtures of dioxane and formic acid which comprises distilling a mixture of dioxane and formic acid in a rectification column in the presence of about one part of an extractive agent per part of dioxane - formic acid mixture, recovering dioxane as overhead product and obtaining the formic acid and the extractive agent from the stillpot, wherein said extractive agent comprises dimethylacetamide and at least one material selected from the group consisting of dodecanedioic acid, isophorone, 2-octanone, 2-methoxy ethyl ether and ethyl phenyl acetate.

* * * * *